US007551078B2

(12) United States Patent  
Carlson et al.

(10) Patent No.: US 7,551,078 B2  
(45) Date of Patent: Jun. 23, 2009

(54) DEVICE ALERT SYSTEM AND METHOD (75) Inventors: Rick Carlson, West Jordan, UT (US); R. Scott Evans, North Salt Lake City, UT (US); Brent Palmer, Sandy, UT (US); Kyle V. Johnson, Murray, UT (US); Vrena B. Flint, Murray, UT (US)

(73) Assignee: IHC Intellectual Asset Management, LLC, Salt Lake City, UT (US)

( * ) Notice: Subject to any disclaimer, the term of this patent is extended or adjusted under 35 U.S.C. 154(b) by 284 days.

(21) Appl. No.: 11/556,089

(22) Filed: Nov. 2, 2006

(65) Prior Publication Data

US 2007/0257788 A1 Nov. 8, 2007

Related U.S. Application Data (60) Provisional application No. 60/746,734, filed on May 8, 2006.

(51) Int. Cl.  
G08B 1/08 (2006.01)  
G08B 29/00 (2006.01)  
A61B 5/00 (2006.01)

(52) U.S. Cl. .................. 340/539.12; 340/506; 340/511; 340/518; 600/301; 128/903

(58) Field of Classification Search ............. 340/539.12  
See application file for complete search history.

(56) References Cited

U.S. PATENT DOCUMENTS

| 4,216,462 | A | 8/1980 | McGrath et al. |
|---|---|---|---|
| 5,576,952 | A | 11/1996 | Stutman et al. |
| 5,724,983 | A | 3/1998 | Selker et al. |
| 5,749,907 | A | 5/1998 | Mann |
| 5,800,381 | A | 9/1998 | Ognier |
| 6,139,494 | A | 10/2000 | Cairnes |
| 6,190,313 | B1 | 2/2001 | Hinkle |
| 6,322,502 | B1 * | 11/2001 | Schoenberg et al. ........ 600/300 |
| 6,336,900 | B1 | 1/2002 | Alleckson et al. |
| 6,366,871 | B1 | 4/2002 | Geva |

(Continued)

FOREIGN PATENT DOCUMENTS

WO WO03103765 12/2003

(Continued)

OTHER PUBLICATIONS

ISR and Written Opinion dated Oct. 26, 2007.

(Continued)

*Primary Examiner*—Donnie L Crosland  
(74) *Attorney, Agent, or Firm*—Snell & Wilmer L.L.P.

(57) ABSTRACT

A system and method for providing a safety alert for a device is disclosed. The invention minimizes or prevents the affects of programming errors and/or provides enhanced alert information to a monitoring healthcare provider, wherein the alert information may relate to a potential safety concern. The method includes monitoring data transmitted from a device and comparing the data to pre-established rules. When the data violates the rules, the system compiles an alert information packet, wherein the alert information packet includes information related to the device and the data. The system then transmits the alert information packet and/or an enhanced alert to multiple computer screens in a particular area.

12 Claims, 5 Drawing Sheets

U.S. PATENT DOCUMENTS

| | | |
|---|---|---|
| 6,443,890 B1 | 9/2002 | Schulze et al. |
| 6,454,705 B1 | 9/2002 | Cosetino et al. |
| 6,542,075 B2 * | 4/2003 | Barker et al. ................ 340/506 |
| 6,579,231 B1 | 6/2003 | Phipps |
| 6,807,965 B1 | 10/2004 | Hickle |
| 6,821,249 B2 | 11/2004 | Casscells et al. |
| 6,893,396 B2 | 5/2005 | Schulze et al. |
| 6,941,271 B1 | 9/2005 | Soong |
| 7,001,334 B2 | 2/2006 | Reed et al. |
| 7,034,691 B1 | 4/2006 | Rapaport et al. |
| 7,081,091 B2 | 7/2006 | Merrett et al. |
| 2003/0009088 A1 | 1/2003 | Korth et al. |
| 2003/0097046 A1 | 5/2003 | Sakamaki et al. |
| 2003/0149344 A1 | 8/2003 | Nizan |
| 2003/0221687 A1 | 12/2003 | Kaigler |
| 2004/0034284 A1 | 2/2004 | Aversano et al. |
| 2004/0044274 A1 | 3/2004 | Bardy |
| 2004/0073098 A1 | 4/2004 | Geva et al. |
| 2004/0087839 A1 | 5/2004 | Raymond et al. |
| 2004/0111014 A1 | 6/2004 | Hickle |
| 2004/0128161 A1 | 7/2004 | Mazar et al. |
| 2004/0225199 A1 | 11/2004 | Evanyk et al. |
| 2004/0236240 A1 | 11/2004 | Kraus et al. |
| 2005/0113705 A1 | 5/2005 | Fischell et al. |
| 2005/0124866 A1 | 6/2005 | Elaz et al. |
| 2005/0190062 A1 | 9/2005 | Sullivan et al. |
| 2005/0256381 A1 | 11/2005 | Santoso et al. |
| 2005/0278073 A1 | 12/2005 | Roth |
| 2006/0015015 A1 | 1/2006 | Kawamoto et al. |
| 2006/0049936 A1 | 3/2006 | Collins et al. |
| 2006/0064020 A1 | 3/2006 | Burnes et al. |
| 2006/0089542 A1 | 4/2006 | Sands |
| 2006/0206011 A1 | 9/2006 | Higgins et al. |
| 2006/0241970 A1 | 10/2006 | Winiarski |

FOREIGN PATENT DOCUMENTS

| | | |
|---|---|---|
| WO | WO2005055112 | 6/2005 |
| WO | WO2006026270 | 3/2006 |

OTHER PUBLICATIONS

Agarwal et al., "Context-Aware System to Create Electronic Medical Encounter Records", Jul. 19, 2006.

University of Michigan, "Small-scale Medical Waste Incinerators: Evaluation of Risks and Best Management Practices", Oct. 2003.

Department of Computer Science, Columbia University, "A SIP-based Medical Event Monitoring System", Jun. 2003.

University of Michigan, "Patient Monitoring: Integrated Dynamic Decision Making in Practice", Jun. 15, 2006.

WWW.PROTOCOL.COM, "Understanding the Wireless Medical Band and the Wireless Medical LAN", May 2001.

* cited by examiner

| Generic Name | Initial Start For Alert To Trigger | Increase That Would Trigger Alert |
|---|---|---|
| Fentanyl | 250 mcg/hr | Rate + > 250 mcg/hr increase |
| Norepinephrine | > 2 mcg/kg/min | > 2 mcg/kg/min |
| Phenylephrine | 200 mcg/min | > 320 mcg/min |
| Vasopressin | 0.05 units/min | |
| Insulin | 10 units/hr | > 100% increase over last rate |
| Propofol | 50 mcg/kg/min | > 100% increase over last rate |
| Heparin | 2500 units/hr | Rate + > 80 mcg/kg/hr increase |
| Epinephrine | 2.5 mcg/kg/min | Rate + > 300 units/hr increase |
| Labetalol | 3 mg/min | > 2.5 mcg/kg/min |
| Amiodarone | 1.5 mg/min | Rate + > 1 mg/min inc. |
| Lorazepam | 2 mg/hr | Anything over 1.5 mg/min |
| Bivalrudin | >0.5 mg/kg/hr | Rate + > 2mg/hr inc. |
| Diltiazem | >10 mg/hr | Rate + 0.5 mg/kg/hr |
| Dobutamine | 9 mcg/kg/min | Rate + 10 mg/hr |
| Dopamine | 9 mcg/kg/min | Rate + 5 mcg/kg/min |
| Eptifibatide | >2 mcg/kg/min | Rate + 5 mcg/kg/min |
| Furosemide | >3 mg/min | (250 mcg/min) |
| Midazolam | >9 mg/hr | Anything >5 mg/kg/min |
| Milrinone | >0.6 mcg/kg/min | Rate + 5 mg/hr |
| Nitroglycerin | >75 mcg/min | Anything >1 mcg/kg/min |
| Nitroprusside | >1.5 mcg/kg/min | Rate + 50 mcg/min |
| Vasopressin | >3 units/hr | Rate + 3 mcg/kg/min |
|  |  | Rate >3 units/hr |

Updated 5/1/2006

DEVICE ALERT SYSTEM AND METHOD

CROSS-REFERENCE TO RELATED APPLICATIONS

This application claims priority to, and the benefit of, U.S. Provisional Application Ser. No. 60/746,734, filed on May 8, 2006 and entitled "Device Alert System and Method," the entire contents of which is hereby incorporated by reference.

FIELD OF INVENTION

The invention generally relates to device alerts, and more particularly, to alerts which minimize the affects of programming errors and/or provide substantive alert information to multiple people.

BACKGROUND OF THE INVENTION

In many industries, it is very important for certain devices to operate appropriately, and for the appropriate amount of materials to be utilized. In some situations, a malfunctioning device or an inappropriate amount of materials may cause significant problems. While an increasing number of machines include safety devices (e.g., automatic shut-off, monitoring gauges, alarms, etc), it is often time-consuming, complicated and expensive to monitor numerous safety devices. More specifically, if the machines are located in different areas, it may not be practical for one person to be able to monitor all the machines at one time. Similarly, one person may be busy or not hear an alarm, so a need exists to notify multiple people of a potential safety problem, and provide various methods of notification.

Moreover, when many machines are in a certain area, it may be difficult to determine which safety device associated with one of the various machines needs attention. Furthermore, if many safety devices are activated at the same time, or a certain safety device often activates, then the perceived "urgency" is often reduced, and the monitoring person may not feel the need to react as quickly.

Many safety devices also include generic alarms without any diagnostic data, wherein the diagnostic data indicates the cause of, or information related to, the safety violation. As such, the monitoring person is not able to quickly determine if the alarm is a critical issue, or a minor malfunction. As a result, the monitoring person typically spends valuable time diagnosing the problem. However, the diagnosis time could be better utilized correcting the problem, particularly if the problem is critical and expanding.

The criticality of monitoring machines and quickly diagnosing problems is highlighted in certain industries where the machines are imperative for survival, such as in the medical field. For example, an incorrectly programmed infusion pump 105 or a disconnection of a ventilator imposes a serious safety threat to patients. Incorrectly programmed infusion pumps 105 or disconnected ventilators may result in a significant number of incident reports and alerts. For example, hundreds of valid pump alerts may occur within a one year period at a single hospital. Some of the incidents may result in a physiological change in a patient due to the incorrectly programmed pump. Furthermore, eExisting infusion pumps 105 (e.g., smart pump technology) do not prevent programming errors based on rate percentage increases or unit specific protocols. Moreover, certain high-risk medications have narrow therapeutic indexes and require careful titration for maximal effect.

Additionally, ventilators may transmit an alarm when a disconnection, breathing pattern change, or leak is detected. Issues related to ventilator alarms may be divided by ventilator use in the ICU and ventilator use in the surgical suite during anesthesia. According to numerous studies, the response times to auditory alarms is significantly shorter than visual alarms since visual alarms require the anesthetists to be looking at the monitor in order to see the alarm. However, a study of 64 anesthetists assessed 10 common operating room alarms for perceived urgency and only 33 percent were correctly identified. (Finley Ga, Cohen A J. Perceived urgency and the anesthetists: responses to common operating room monitor alarms. Can J Anaesth. 1991; 38(8):958-64.) Another study that focused on the complications of mechanical ventilation in the ICU, listed the repeated sounding of the ventilator alarms (false positive alarms) as a major reason why clinicians are called to the bedside. (Keith R L, Pierson D J. Complications of mechanical ventilation. A bedside approach. Clin. Chest Med. 1996; 17(3):439-51.) An Australian study of 2,000 incident reports identified 317 incidents that involved problems with ventilators and the majority (47%) was caused by disconnections. (Russell W J, Web R K, Van der Walt J H, Runciman W B. The Australian incident monitoring study. Problems with ventilation: an analysis of 2002 incident reports. Anaesth. Intensive Care. 1993;21(5): 617-20.) A study to determine the predictive value of alarms from pulse oximeters, end-tidal PCO2 monitors, ventilators, and electrocardiographs in a pediatric ICU found that 68% were false and the positive predictive value for ventilator alarms was only 3%. (Lawless ST. Crying wolf: false alarms in a pediatric intensive care unit. Crit Care Med. 1994; 22(6): 981-5.) Likewise, another study found that of 1,455 alarm soundings in the ICU, only 8 (0.5%) indicated potentially life-threatening problems. (O'Carroll T M. Survey of alarms in an intensive therapy unit. Anesthesia. 1986; 41(7):742-4.)

While the alarm systems built into all ventilators today have become very accurate at identifying critical events (Bender H J, Frankenberger H, Ryll C, Albrecht M D. The performance of respirator alarms during simulated critical events in CMV/IPPV artificial respiration. Anesthesist. 1993; 42(6):365-75. Kacmarek R M, Meklaus G J. The new generation of mechanical ventilators. Crit Care Clin 1990; 6(3): 551-78.), too often the resulting alarms go unnoticed for excessive periods of time. This results from a system problem that is outside of the control of the ventilator. This may be due to, for example, the physical layout of the ICU, staffing limitations, staff complacency due to numerous false alarms and/or environmental acoustics and noise. Another serious problem is when patients who are in isolation for infection experience a critical ventilator event. The closed doors can prevent hospital personnel outside the room from hearing or seeing standard ventilator alarms. (Morganstern M S, Karpel S K. Modification of an external low-pressure ventilator alarm to allow its remote use for isolated patients. Respir Care. 1986; 31(5):395-401. Stelfox H T, Bates D W, Redelmeier D A. Safety of patients isolated for infection control. JAMA 2003; 290:1899-905.) In some situations, the ventilator alarm is heard, but valuable time can be lost while the clinician tries to determine which patient or room in the unit activated the alarm. Moreover, current systems do not provide respiratory care management with information on the duration of the critical events, especially with regard to ventilator disconnections.

A need exists for a system and method that minimizes or prevents the affects of programming errors, and/or provides more specific safety violation information to multiple healthcare providers and/or locations.

SUMMARY OF THE INVENTION

The present invention includes a system and method for providing an enhanced safety alert for a device. The invention minimizes or prevents the affects of programming errors and/or provides more specific alert information to a monitoring person, wherein the alert information may relate to a potential safety concern. The method includes monitoring data transmitted from a device (e.g., infusion pump, etc) and comparing the data to pre-established rules. When the data violates the rules (e.g., a programming rule based on rate percentage increases, unit specific protocols, etc.), or triggers an internal alarm (e.g., breathing changes, disconnections, etc.), the system compiles an alert information packet, wherein the alert information packet includes information related to the device and the data. The system then transmits the alert information packet to multiple healthcare providers, locations, and/or communication devices (e.g., multiple computer screens in a particular area).

BRIEF DESCRIPTION OF THE DRAWINGS

Additional aspects of the present invention will become evident upon reviewing the non-limiting embodiments described in the specification and the claims, in conjunction with the accompanying figures, wherein like numerals designate like elements, and wherein:

DETAILED DESCRIPTION

The detailed description of exemplary embodiments herein makes reference to the accompanying figures, which show the exemplary embodiment by way of illustration and its best mode. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

In general, the present invention facilitates minimizing or preventing the affects of programming errors (e.g., incorrect rate increases or excessive initial doses). In other embodiments, the invention also facilitates providing enhanced and more specific alert information to a monitoring person, wherein the alert information may relate to a potential safety concern related to materials or a machine. The safety concern may include, for example, excess material, insufficient material, inaccurate dosages, inappropriate titration (rate changes), uneven flow, undesired operational changes, inappropriate times, improper disconnections, obstructions, physiological changes, breathing changes and/or any other measurable quantity or feature.

A "safety concern" or similar phrase, as used herein, does need to necessarily relate to safety and it may relate to any item, device, material, software, hardware, person, organization, company and/or the like that may be monitored. As used herein, "materials" may relate to one or more of medicine, physiology, body fluids, breath, blood, fluids, heat, coolant, air flow, lubricant, power, stability (e.g., vibrations, earthquakes, etc), environmental factors (e.g., humidity, dew point, rain) and/or the like. The "monitoring person", as used herein, may include any person, group, device, software, hardware, organization, company and/or the like that may help with any portion of the monitoring, correcting or fixing process. The "machine" as used herein, may include any device, hardware, software, entity, person, company and/or any other device which may be monitored for a safety concern. In exemplary embodiments, the machine may include an infusion pump 105 or a ventilator. As used herein, a healthcare provider may include any software, hardware, entity or other person such as, for example, one or more of: a physician, nurse, technician, respiratory therapist, hospital staff, administrator, monitoring person and/or any other person.

By providing more specific alert information, the present invention reduces the time to identify and/or prevent patient harm, reduces the amount of work hours and people used to monitor safety devices, simplifies the monitoring process and reduces the cost and administrative issues related to monitoring numerous safety devices. More specifically, if the machines are located in different areas, one person may be able to monitor all the machines at one time. Similarly, the invention allows many people to help monitor the machines because the notification is sent to multiple communication points (e.g., computer screens), so the healthcare provider that is more available can respond to the safety concern.

When many machines are in a certain area, the invention facilitates determining which safety device associated with one of the various machines needs attention. Furthermore, if many safety devices are activated at the same time, or a certain safety device often activates, the notification information focuses the responder on a particular safety device, and the level of seriousness of the safety concern. The notification information also reduces the time needed for diagnosing the problem, so the responder can better utilize her time correcting the problem, or with other important work related functions. In other words, the notification information or alert packet may include data or information related to the correct or incorrect operation of the machine, or to a safety concern, thereby allowing the monitoring person to focus his efforts on a particular area of the machine.

Using the medical field as an example, and specifically, an infusion pump 105 as the device, the present invention alerts healthcare providers whenever an infusion pump 105 dosage or rate change is outside specified parameters. The pump alert program of the present invention helps reduce the number and severity of pump programming errors. Implementation of an alert system to identify inappropriate medication rate changes in an ICU enables hospitals to prevent potentially severe adverse drug events. Data from alerts may be analyzed and used to improve programming logic and/or educate on proper pump or drug utilization. Some of these alerts helped identify improper charting and process errors.

Figure 1:
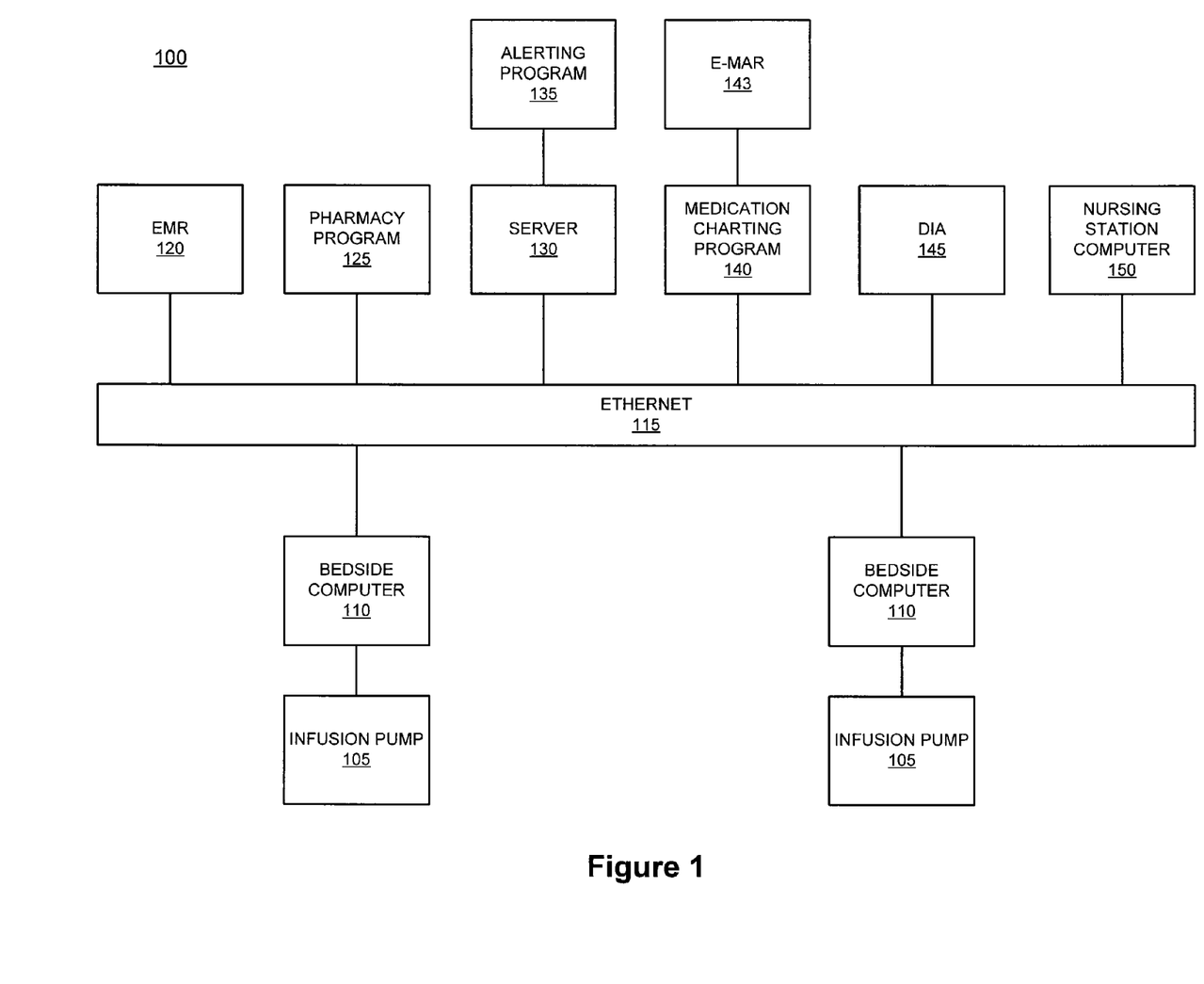
FIG. 1 shows a diagram of an exemplary enhanced pump alerting system in accordance with exemplary embodiments of the present invention.

In an exemplary embodiment, and with respect to FIG. 1, the system 100 includes at least one of: a pharmacy program 125, a medication charting program 140, a device information acquisition (DIA) program 145, and/or an alerting program 135. System 100 may communicate with the various components and/or programs via an Ethernet 115, or any other communication system discussed herein. Pharmacy program 125 includes any hardware and/or software that is suitably configured to generate medication orders for a patient. Medication charting program 140 includes any hardware and/or software which is suitably configured to associate a medication to an infusion pump 105 and/or to chart the volume infused. In one embodiment, medication charting program 140 includes an electronic medication administration record (e-MAR 143) which records pump dosage and rate changes into the patient's e-MAR 143.

If a healthcare provider (e.g., nurse) fails to associate a drip to e-MAR 143, the pump may be mis-programmed. As such, the system is linked to the e-MAR 143, thereby becoming a powerful tool to monitor and alert healthcare workers to many other pieces of information. Because it is linked to e-MAR 143, system 100 creates alerts that are specific for patient's current disease states such as sepsis, stroke, or traumatic brain injury. The system also monitors (based on age, co-morbidities, pregnancy status, and even screening criteria such as the Beers Criteria) for potentially inappropriate medication use in older adults. By linking this system to e-MAR 143, system 100 can monitor any prescribed medication, not just those medications in a specific drug library.

Figure 2:
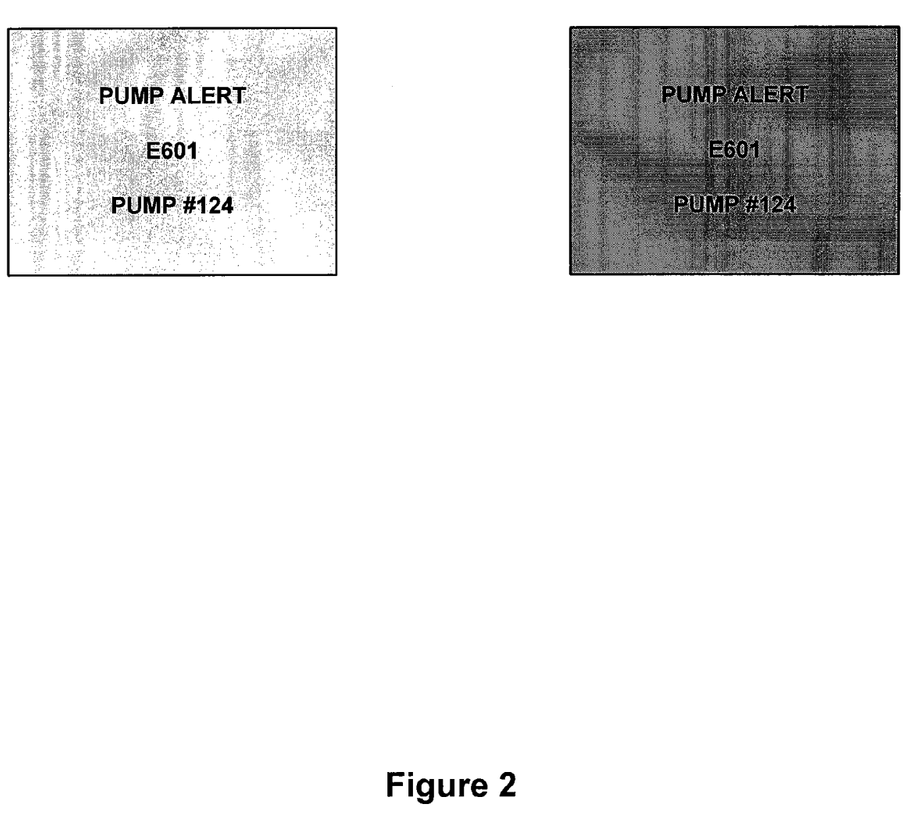
FIG. 2 shows an exemplary display which is sent to every computer in the same unit as the patient with a pump alert in accordance with exemplary embodiments of the present invention.

DIA program 145 includes any hardware and/or software that is suitably configured to update and/or record the status of each infusion. The DIA 145 is an interface between infusion pumps 105 (e.g., Alaris Infusion Pump) and the e-MAR 143. Infusion pump 105 may be interfaced to bedside computer 110 (e.g., via IEEE 1073), and bedside computer 110 interfaces with ethernet 115, thereby allowing infusion pump 105 to send data to any of the components and programs of system 100. By linking the infusion pumps 105 to the e-MAR 143, parameters can be very sophisticated, complex, and patient-specific. DIA 145 automatically records pump rate changes and other information in the e-MAR 143. As such, DIA 145 alerts the healthcare provider about pump programming errors, such as, for example, infusion pump 105 dosages or rate changes falling outside specified parameters. If an infusion pump 105 has been set to a dose rate that exceeds the limits from the medication rules, then DIA 145 is configured to send an alert information packet to the alerting program 135 which displays the alert information (as shown in FIG. 2) on nursing station computers 150.

By linking the DIA 145 interface to infusion pumps 105 and e-MAR 143, pump 105 is a smarter pump and system 100 is a smarter system. System 100 may assist in improving several areas including patient and nurse safety, accurate charting, and providing education and information on safe and proper use of these high-risk medications. The system may also run in tandem with "smart" pumps and provide additional information and safety measures that the smart pumps are not capable of providing or do not provide sufficiently.

Alerting program 135 includes any hardware and/or software that is suitably configured to track certain computers' demographics (e.g., if the computer is alert enabled, location, IP address, etc) such that the system knows which computers are in the unit where the alert occurs. In another embodiment, alerting program 135 includes a client application that resides on each nursing station computer 150 and/or other computers in the unit. The client application is configured to monitor for alert information packets and receives the alert information packets. Upon receipt of the alert information packet, the client application is configured to activate the alert screen or close the alert screen.

The methods and process flows described below are merely embodiments and are not intended to limit the scope of the invention as described herein. For example, the steps recited in any of the method or process descriptions may be executed in any order and are not limited to the order presented. It will be appreciated that the following description makes appropriate references not only to the steps and user interface elements, but also to the various system components as described above.

As will be appreciated by one of ordinary skill in the art, the system may be embodied as a customization of an existing system, an add-on product, upgraded software, a stand alone system, a distributed system, a method, a data processing system, a device for data processing, and/or a computer program product. Accordingly, the system may take the form of an entirely software embodiment, an entirely hardware embodiment, or an embodiment combining aspects of both software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

Figure 4:
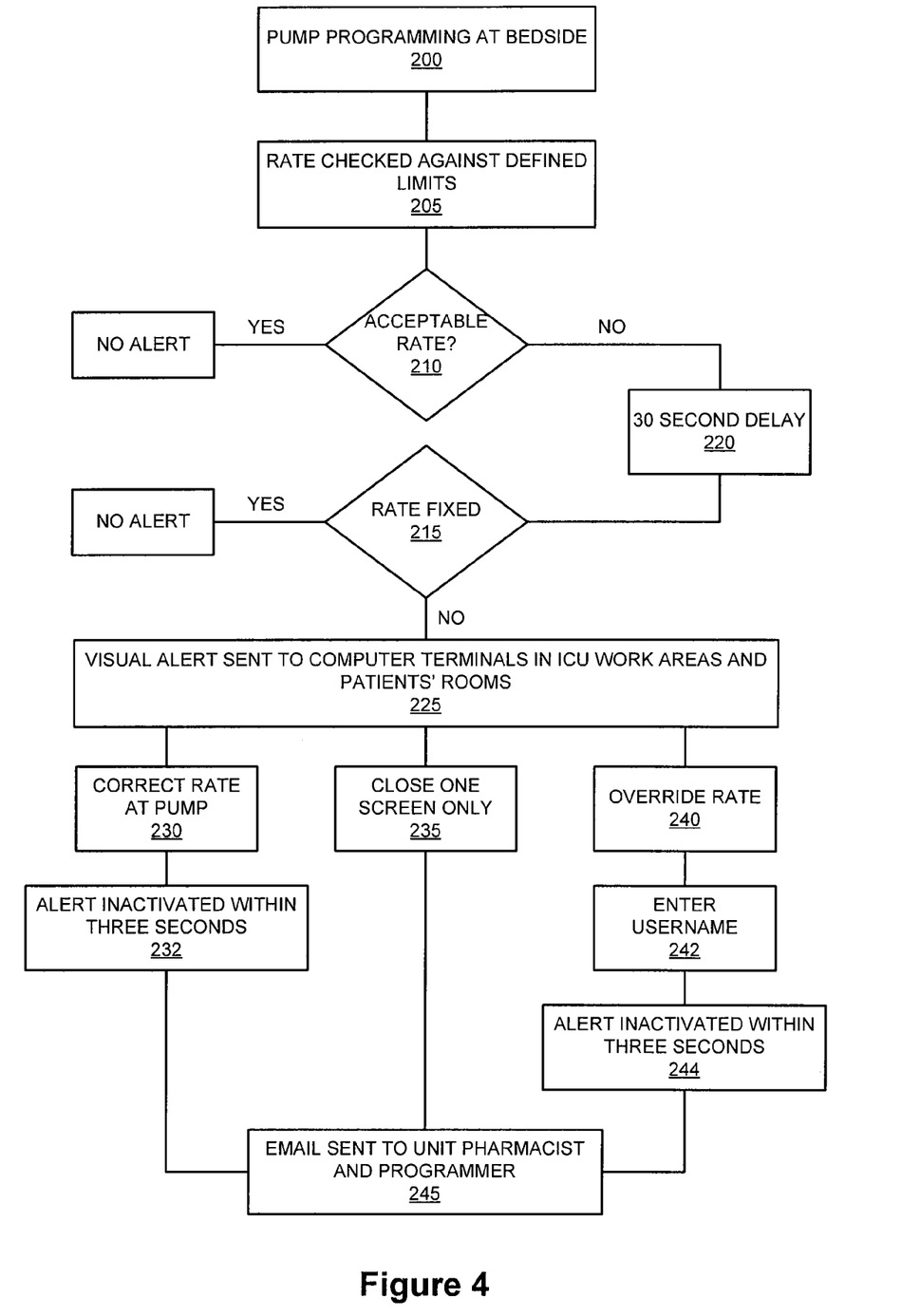
FIG. 4 shows a flow chart of the monitoring and alerting method in accordance with exemplary embodiments of the present invention; and, FIG. 5 shows a diagram of an exemplary ventilator enhanced alerting system in accordance with exemplary embodiments of the present invention.

After a healthcare provider (e.g., physician) drafts an order for certain medicine or fluid for a particular patient, the pharmacist enters the order into pharmacy program 125. Medication charting program 140 then obtains the order information and presents the medication order to another healthcare provider (e.g., nurse) via any network or communications device discussed herein. With respect to FIG. 4, the nurse obtains the infusion bag with the ordered medication, programs the pump at bedside (step 200) and starts the infusion into the patient. The nurse enters information (e.g., medication, start time, and other data) into the medication charting program 140. For example, with respect to the administration of Heparin, a nurse may enter into medication charting program 140 that she is administering 1000 units per hour of Heparin at 0900 hours (concentration is 25,000 units per 250 mLs). This would equal a rate of 10 mLs per hour. The DIA 145 then obtains the information from the medication charting program 140. DIA 145 also obtains the rate information from infusion pump 105, then consolidates the pump data with the information obtained from medication charting program 140. DIA 145 then compares the consolidated information with the rules and parameters (step 205).

Figure 3:
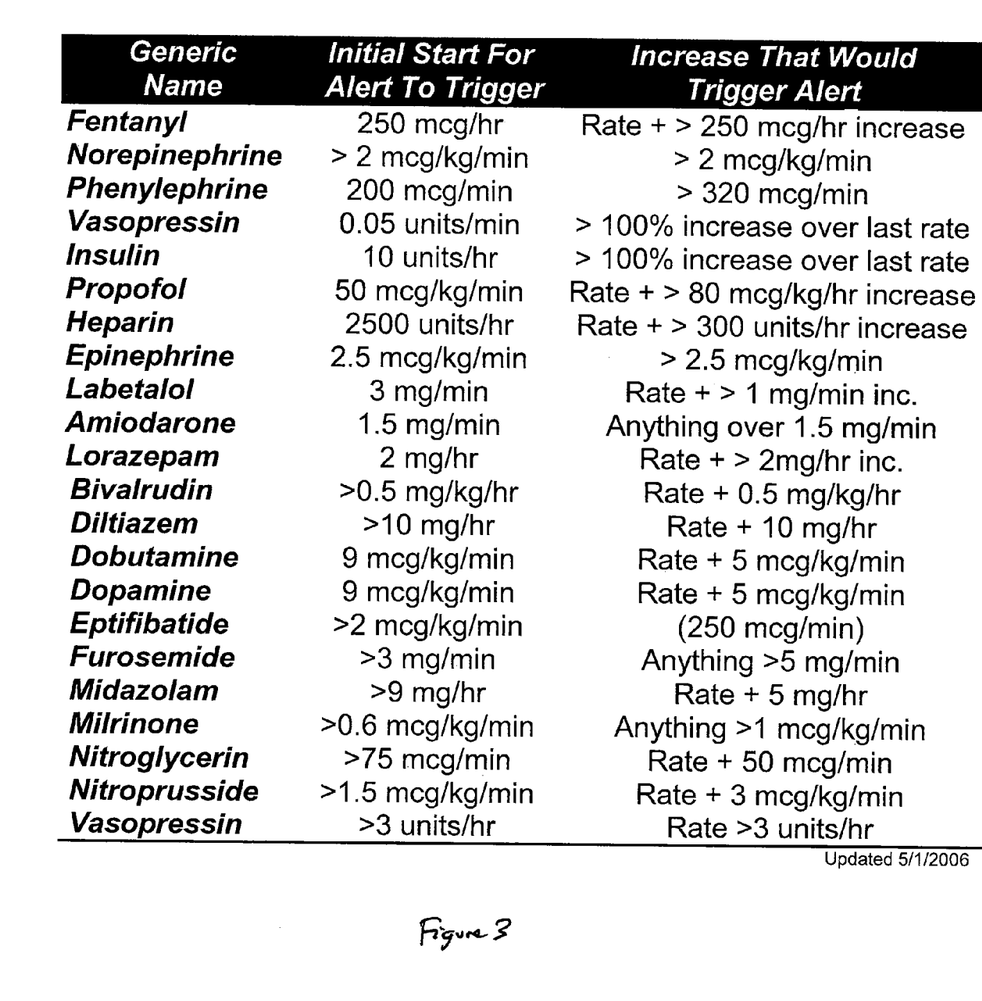
FIG. 3 shows exemplary rules for certain medicines in accordance with exemplary embodiments of the present invention.

In one embodiment, the rules are implemented for certain medications that may be considered high risk for programming errors (FIG. 3). The rules and alerts may include considerations to limit alerts when hanging a new bag with a higher rate after a lower rate (e.g., KVO rate), and how medications are used for critically ill patients. Each medication is assigned a rate limit (FIG. 3) and the pump alerts are based on the rate limits which may include the maximum initial rate or maximum rate change considered safe. Initial rate triggers include, for example, fixed infusion rates, whereas rate change triggers include for example, percentage increases, fixed rate changes, or maximum infusion rates. Some trigger rates are based on protocols in use in the ICU (e.g., insulin or heparin protocols). In other embodiments, patient specific information from the e-MAR 143 is included when evaluating medication dosages and rates based on disease states, age, co-morbidities, and other pertinent information. If an infusion pump 105 has been set to a dose rate that exceeds the limits from the medication rules (step 210), the system may include a 30 second delay (step 220) before checking to determine if the rate has been fixed (step 215). If the inappropriate rate is not fixed, then DIA 145 sends an alert information packet to the alert program. The alert information packet is also sent to a database via a network.

When an error is identified, the system generates a visual alert that is displayed (as shown in FIG. 2) on one or more computer screens in the same unit (e.g. ICU) as the person with the pump alert and/or patient rooms (step 225). The alerts may also be transmitted via any network to other computers, personal digital assistants, IP addresses, pagers, emails, and/or via any other hardware or software known in the art, or discussed herein. In an exemplary embodiment, the alert information packet includes patient demographics, percentage increases to unit protocols and/or the like.

In another embodiment, if a "Keep Vein Open" (KVO) order exists for a maintenance IV, then the system may send an alert if the infusion bag is dry after 45 seconds. The screen color may alternate, for example, from blue and black every two seconds. The alert may also cause any other visual, audio, physical (e.g., vibration) or other notification, wherein the notification can increase in volume, intensity, random changes, increasing changes, decreasing changes, and/or the like. DIA 145 may also send an email with the alert information packet to any desired individual or system.

For example, in addition to the visual alerts, all pump alerts and pump corrections create one or more automatic emails. The email may be sent to the study pharmacist (e.g., in the unit where the alert occurred) (step 245). The email may include one or more of the following information: patient name, patient ID number, room number, pump number, drug, initial rate, rate before and after the alert, medication name and/or the like. The emails may also provide information related to overrides, what action was taken to inactivate the alarm (i.e. corrected the rate or clicked to override the alarm), and, if override was chosen the username would be provided. The study pharmacist has the opportunity to act upon on all alerts and evaluate the appropriateness of each alert. Rate limits are adjusted as needed, and users are educated on proper use of the high risk drugs when appropriate.

In one embodiment, the email may state: "Pump-Medication Alert Activated 2006 Aug. 8 06:20:21, E601, Patient ID #, 305, Fentanyl, 1500.0, 100.0, 5, 14 2006 Aug. 08 06:20:52, Alert Fixed room: E601; division: STRI; deviceNumber: 305; med: Fentanyl; rate: 15.0; previousRate: 150.0; orderNumber: 5; bottleNumber: 14." This e-mail may be interpreted as: This alert occurred Aug. 8, 2006 at 06:20:21 in room E601. It then gives the patients ID number followed by the pump number. The medication was fentanyl and the rate was changed to 1500 mcg/hr from 100 mcg/hr. It is order number 5 and was the fourteenth bag on this order. The alert fix occurred Aug. 8, 2006 at 06:20:52. The rates in the second e-mail are recorded as ml/hr. The nurse "fixed" the alert by going to 15 ml/hr from 150 ml/hr. In one embodiment, these arrive in two separate e-mails.

In some embodiments, alerts are terminated by (i) correcting the infusion dosage or rate at the pump (step 230); (ii) overriding the alert from the computer screen if the user feels the rate is appropriate (step 240) (the user may be prompted to enter a user name and/or password before the screen will clear (step 242)); and/or (iii) close the alerting message on the specific terminal only (step 235), while the other terminals continue to display the alert until the other options are selected. In one embodiment, actions (i) and (ii) restore all computer screens to their previous state within a particular timeframe (step 232, 244). The invention also enables the first responder to send a notification to other potential responders (via any network or communication device discussed herein) that the safety violation is being handled to avoid unnecessary duplicative responders.

More particularly, in one embodiment, an intravenous drip is ordered by a physician. The pharmacist schedules the medication in tandem and the medication arrives at the floor. A nurse hangs the IV medication on the infusion pump. When starting the initial IV drip there is a maximum rate built in such that, if that maximum rate is exceeded, the alarm is triggered. During subsequent dose adjustments, the alarm would be triggered if the dose exceeded a specific percentage increase over and above the last running rate. (FIG. 3). If an incorrect infusion rate was set, the nurse would have 30 seconds to correct the incorrect infusion rate before an alarm would be activated. If, after 30 seconds, the infusion rate has not been corrected, an alarm would be activated and would not be inactivated until the rate has been corrected and/or additional steps had been taken. An e-mail would also be sent to the pharmacist notifying him/her of an incorrect infusion rate. The pharmacist would then follow up with data collection regarding the event and evaluate for process improvements.

The alarm description includes, in one embodiment, a visual alarm tied to the infusion pumps 105 and the computer screens in, for example, the Shock Trauma (STRI) nursing area. This visual alarm would be a blue color (similar color as the Alaris infusion pumps 105). The color would be solid blue and would flash on and off on all of the computer screens in the STRI unit. This flashing screen with the alert information would be a visual alert to the nursing staff that a pump error has occurred and further action needs to take place. Information that would be included with the flashing screen would include one or more of: patients room number; "pump error" statement; the pump number; an option to close the screen; an option to override the pump error and turn off the alarm; this override would last until a new rate change outside of the specified limits was exceeded at which time it would alarm again; and, if override option is chosen a box would appear that would allow the user to free text in their name.

The healthcare provider may also inactivate the alarm, in one embodiment, by correcting the infusion rate to be within the proper limits either below the maximum initial infusion rate allowed if hanging a new IV bag or if changing the current infusion rate to be within the maximum percent increase over the last appropriate running rate. In another embodiment, an option exists to override the "incorrect" infusion rate, thus giving the user control over infusion rates that occasionally run at rates outside defined limits. If override is clicked, a box would appear that instructs the user to enter their name before allowing them to proceed and inactivate the alarm. Once the pump error is corrected, or alert is overridden, the alert lasts about less than 3 seconds before shutting off. After correction or overriding, a second email (or multiple emails) may be sent to the same and/or different persons. The second email may include the override information and the person who performed the override, if applicable.

In another embodiment, an option on the screen exists to minimize the specific screen or close all the screens, thus inactivating the alerts on all screens. If the user chooses to minimize the screen, it would only inactivate the alert for that specific computer screen and allow a computer user not associated with the room to continue using the computer without more interruption. Minimizing the specific screen does not disarm the alert for the other screens in the unit. If the user chooses to close the screen and inactivate all the alerts the "Override" message appears to require them to choose override and enter their username.

As a specific example, a patient in the ICU may be ready to be extubated. The healthcare provider (e.g., physician) writes an order for extubation and to turn the fentanyl drip down from 100 mcg/hr to 75 mcg/hr. Upon extubation, the patient also experiences some stridor and is treated appropriately. The nurse turns the fentanyl drip down to 75 mcg/hr. The screens in the ICU begin to flash with a pump alert for that patient's room. Several nurses and the pharmacist respond to the room and find the pump running at 75 mLs/hr or 750 mcg/hr. With the 30 second delay built into the program and the time to respond to the alert, this patient received an extra 8.5 mcg fentanyl. Before the pump alerts of the present invention, this situation may have gone unnoticed and required reintubation or caused other physiological harm to the patient.

In another example using insulin, when the ICU is busy in the early morning hours, one healthcare provider (e.g., nurse) may ask another nurse to check her patient's blood glucose. The second nurse checks the blood glucose and it is 102 mg/dl. The insulin drip protocol instructs the nurse to increase the drip rate from 2.8 units/hour to 3.2 units/hour. When programming the infusion pump, the nurse may still be thinking about the blood glucose, so she programs the pump at 102 units/hour. After thirty seconds, the alerts are activated. Several nurses respond to the patient's room and find the pump to be running at 102 units/hour, so they can immediately correct the error. In this example, the patient received an extra 2.3 units of insulin due to the mis-programmed infusion pump. Before the pump alerting program 135 was installed, this patient may have received the complete bag of insulin, 100 units, in just under one hour. Hypoglycemia can be avoided and patient care resumed.

In another example, a patient is on fentanyl drip at 100 mcg/hr. The nurse wants to decrease the rate from 100 mcg/hr to 80 mcg/hr. The pump was programmed and the nurse walked into the rounds room to round on her patient. An alert occurred. The charge nurse walked into the room and checked the pump. It was set on 80 mLs/hr or 800 mcg/hr. Charge nurse put the pump on hold, went and found the nurse for the room and asked if they really wanted to be giving the patient 800 mcg/hr of fentanyl. The drip was decreased to 80 mcg/hr (8 mLs/hr). The total time between changing the pump to 800 mcg/hr to the correct rate of 80 mcg/hr was approximately 1 minute 47 seconds. This includes the 30 second delay before the alert occurred and the time the pump was on hold. Calculated out the patient received 14.6 mcg fentanyl in that 1 minute 47 seconds. The fentanyl bag has 1000 mcg total. Potentially the patient could have received a max of 1000 mcg which, at the incorrectly programmed rate, they would have received it over 1 hour 15 minutes. The current rate of fentanyl for this patient was 80 mcg/hr.

In another example, the patient was on a lorazepam continuous drip at 0.5 mg/hr or 5 mLs/hr. A student nurse was working with the nurse for that room for the day. The student nurse was a nurse that currently worked on a floor in another area of the hospital and was going to school. The pump was beeping. The student nurse went into the room and the volume to be infused (VTBI) was at 0. There was still volume in the bottle and so the button was pushed and the VTBI was changed to 15 more mLs. The lorazepam drip was programmed on the pump to use the dose rate calculator (DRC). When it is programmed like this, the button to change the VTBI is now the button to change the rate and the VTBI button is below the rate button. The student nurse actually changed the rate to 15 mgs/hr, and then when the pump still did not work, she looked closer and changed the VTBI to 15 mLs and hit run on the pump without changing back the rate. Since the VTBI was 0, the pump would have read 5 mLs/hr before hitting run again. An alert occurred and the nurse for the room went in and discovered the problem. The pump ran at 15 mgs/hr for a total of 1 minute and 45 seconds. This includes the 30 seconds it took for the alert to occur and another 75 seconds to fix the problem. Regardless, the patient received a total of 0.44 mg lorazepam extra during that time. The lorazepam drips have a total of 10 mg in the bottle. They would have received that in 40 minutes at the current rate. Patient was only on 0.5 mg/hr before rate change occurred.

In still another example which reduced the impact of a pump error, a patient was on a fentanyl drip at 100 mcg/hr. The patient was just extubated and sedation needed to be decreased to keep the patient from being too sedated and requiring re-intubation. The drip was to be turned down to 75 mcg/hr. An alert occurred. The pharmacist was sitting at a computer terminal just outside the room and went in to check on the pump. Pump had been incorrectly programmed for 750 mcg/hr or 75 mLs/hr. The nurse had been rather busy and also had a student nurse they were responsible for that day and had several people talking to them at once. The patient received fentanyl at 750 mcg/hr for approximately 40 seconds. That equates to approximately 8.5 extra mcg of fentanyl. This could have been potentially harmful to the patient. Since she was just extubated, any excess sedation could have caused her to not be able to protect her airway and may have required her to be re-intubated. Patient also experienced stridor on extubation requiring inhaled racemic epinephrine.

In another example, the patient was on 150 mcg/hr fentanyl and the rate was changed to 500 mcg/hr. The nurse again was thinking in mcg/hr and programmed mLs/hr. Instead of going to 50 mcg/hr from 150 mcg/hr, the nurse went to 50 mLs/hr or 500 mcg/hr.

With respect to KVO rates, in another example, a patient may be on a very high dose of norepinephrine to maintain an adequate blood pressure. If the bag runs dry, the pump automatically goes to a KVO rate of 5 ml/hr. The audible sounds from the pump may not be heard, and the patient's hemodynamic status may start to decompensate. Only after the empty bag is eventually noticed and replaced will the patient's hemodynamics be stabilized. Because of this experience, the invention allows the hospital to program "KVO Limits" into the pump alerting programming logic. In one embodiment, if one of the infusions is running above a certain determined rate, and then goes to a KVO rate for greater than 20 seconds, the pump alert screens will be activated. This feature may only be activated on the cardiac medications and propofol.

In various embodiments, the invention includes the specificity of being able to tie alerts into unit-specific protocols. For example, heparin and insulin limits may be specific to unit protocols. The invention allows a hospital to educate on the importance of having and following unit-specific protocols. For example, different protocols may exist for heparin among the different ICUs, thereby resulting in numerous alerts related to heparin infusions being generated. As such, a hospital would be able to modify the heparin drip protocol making it a standardized protocol throughout the facility.

The invention also improves the accuracy of electronic charting. A healthcare provider (e.g., nurse) often starts a new medication on a pump that was still associated with the previous medication that had been infusing through that pump. For example, with a patient on an insulin drip that had been turned off, the nurse may go to the patient's room to give a dose of vancomycin and use the infusion pump 105 that had previously been used for insulin. The rate was set for 250 ml/hr. Because vancomycin is a piggyback, it does not need to be associated with e-MAR 143 and gets charted as a single dose given. However, with the pump still being associated to the insulin drip, the program records insulin as running at 250 units/hour. With the pump alert system of the present invention, an alert occurs within 30 seconds of starting the infusion. The nurse can then disassociate the pump from the previous medication and the medical record is accurate and complete. As such, the present invention improves the accuracy and completeness of medication charting.

The alerts may also keep the patients from receiving supra-therapeutic doses of high-risk medications. Other alerts may result in: improved medication charting, stopping the practice of bolusing high-risk medications through the pump, educational efforts on proper use of medications, KVO-related events, some false positive alerts and/or the like. Many of the alerts may also occur by programming in ml/hr, rather than the desired dose. For example, fentanyl is by far the most frequently mis-programmed medication. The error usually occurs when the healthcare provider is thinking in mcg/hr and programs the dose into the pump as ml/hr. The potential for error is compounded because of the high number of distractions that are common in the ICU, which the nurses encounter almost daily. Programming errors also occur when student nurses manipulate the pumps or newly hired nurses program the pumps in error. These practitioners are usually not familiar with specific infusion devices. As such, the present invention serves as another safety mechanism to protect the students and the patients.

Because the invention may be an enhancement to the DIA 145 interface, the system enables collection data on any infusion pump 105 that is associated with, or interfaced to, e-MAR 143. Numerous ICUs may use this same interface. Although the programmer and the pharmacist may not have flashing screens to alert them to an error, the system enables collection in a database of pump programming errors via the e-mails that are sent to the programmer and the pharmacist.

The data may also provide a global look at how infusions are being used in other ICUs. For example, if an e-mail is received that shows heparin running at 1800 units/hour, then it goes to 9999 units/hour, and a few minutes later to 1950 units/hour, the patient may have a sub-therapeutic activated partial thromboplastin time (aPTT). Instead of giving a subcutaneous bolus of heparin, the healthcare provider can chose to just increase the rate of the pump for a few minutes and call it a bolus. If an e-mail shows propofol running at 20 mcg/kg/min, and then it goes to 1344 mcg/kg/min for several minutes before returning to 25 mcg/kg/min, it may indicate that the nurse is using the infusion pump 105 to give a bolus, a potentially dangerous practice. This information may be shared with the unit managers, and a safety standard developed for all ICUs on the appropriateness of bolusing medications. This standard may call for boluses to be given as separate injections, and not to be completed with the infusion pumps 105.

Again using the medical field as an example, but this time specifically using a ventilator device as the device or machine, the present invention provides an enhanced alerting system which provides healthcare providers an enhanced alert whenever inappropriate breathing changes occur, obstructions are detected, disconnections exist and/or other ventilator concerns exist. Most ventilators are now designed to detect critical events and are equipped with alarms. However, as discussed above, the alarms are often ignored, not heard, or often activates, so the perceived "urgency" is often reduced. The ventilator alert program of the present invention helps reduce the number and severity of ventilator errors. The enhanced alert system in an ICU has enabled hospitals to prevent potentially severe adverse events. Data from alerts may be analyzed and used to improve procedures and/or educate staff on proper ventilator connections and breathing patterns. Some of these alerts also help identify improper charting and process errors.

The enhanced alert system monitors ventilator systems, and receives information from the ventilator internal system after the ventilator internal system identifies inappropriate breathing changes, disconnections of ventilator tubes and/or other ventilator concerns. In an exemplary embodiment, the system uses the Puritan-Bennett 840 or 7200 mechanical ventilators. This ventilator manufacture defines critical ventilator events as when less than 25 percent of the gas delivered by the ventilator is returned to the ventilator and classifies them as "ventilator disconnections". Thus, the ventilator circuit may or may not be physically disconnected when a disconnection alarm is generated.

The common exemplary causes for a reduction in the amount of gas returning to the ventilator include the following: (1) Disconnection of the ventilator circuit (e.g., circuit becomes detached from the patient's artificial airway, pieces of the circuit become disconnected from each another); (2) During a medical procedure the ventilator is disconnected intentionally. However, the staff forgot to ventilate the patient, or forget to turn off the ventilator as alternative ventilation is being provided; (3) Obstruction of the tubing connecting the patient to the ventilator (e.g., condensed water filling the tubing, kink or blockage in the tubing, leak in the tubing, etc) (4) The patient's artificial airway comes out accidentally (extubation); (5) Leak around the artificial airway (cuff leak); (6) Obstruction of the patient's artificial airway; (7) Leakage through the outside surface of the lung (bronchopleural fistula); (8) The patient takes multiple breaths from the ventilator in a row without exhaling between breaths. This generally occurs when the ventilator is delivering only small-sized breaths to the patient, but the patient is trying to get much larger breaths (breath-stacking or patient-ventilator dyssynchrony).

Figure 5:
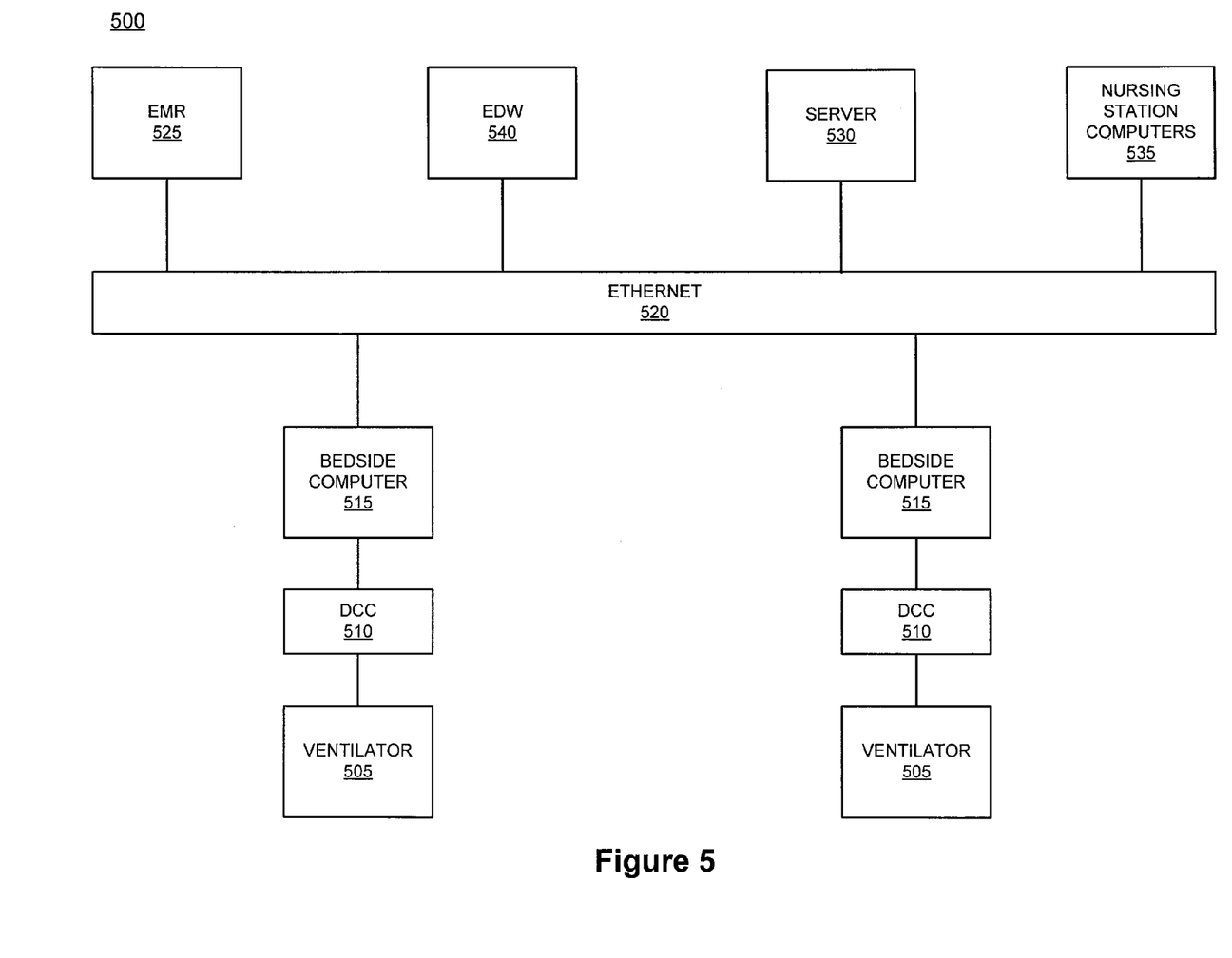

In an exemplary embodiment, and with respect to FIG. 5, the enhanced ventilator alert system 500 includes an external microcomputer, a Device Communications Controller (DCC) 510 that is connected to the ventilators through, for example, an RS232 connection. DCC 510 polls the ventilator 505 (e.g., every five seconds) and the ventilator sends current alarm and ventilator settings. DCC 510 then sends ventilator data, including whether the alarm silence button on ventilator 505 had been activated, to bedside computer 515 using, for example, the IEEE MIB 1073 standard. Bedside computers and the other components of the system 500 interface via Ethernet 500 or any other communication protocol or device discussed herein. Bedside computer 515 accesses EMR system 525 to determine which room the computer is located, along with other pertinent patient information. Bedside computer 515 parses the data string from the ventilator and attaches the patient room number. In one embodiment, if the ventilator sends three consecutive disconnection alarms to DCC 510 and the alarm silence status of the ventilator is "off", bedside computer 515 sends an alert to a central server 530 through Ethernet connection 500 using TCP/IP. Because DCC 510 polls ventilator 505 every five seconds, the disconnection alarm on the ventilator is active for at least 10 seconds before the enhanced alert is generated. If the silence button on the ventilator is pressed by a healthcare provider (alarm silence) or the ventilator-disconnect alarm is no longer active, then a message is sent to the server to turn the alert off. Thus, three different messages are sent from the bedside computer to the server: 1) activate alert, 2) ventilator alarm was silenced, and 3) ventilator event was corrected. If the silence button is pushed on the ventilator and the disconnection alarm is still active for a period of time (e.g., for two or more minutes), an activate alert message will be resent to server 530.

The present invention significantly reduces or eliminates false-positive enhanced alerts because the program on DCC 510 distinguishes between the severity and different types of alarms generated by ventilator 505. Because users will not tolerate many false positive alarms, the lack of false positive enhanced alerts is a key factor leading to high clinician acceptance of the present invention.

With the enhanced alerting system 500, respiratory care management is provided the information they need to perform root-cause analyses on each of the types of critical ventilator events. Each time the new enhanced ventilator alert is activated, healthcare providers are prompted by the computer charting program to review the event. Moreover, the therapists are now notified of most or all critical events, whereas previously, many events were handled by other medical staff and not reported to respiratory care. The information provided by the new report allows the health care team to see trends as to whether patients are restrained properly, patient breathing tubes are secured, circuits are being drained of water, whether staffing is sufficient and whether alarms are answered in a timely manner. There is also a check to see whether the right members of the health care team are notified of the critical events.

Some ventilator events, including those that occur during procedures, are generally not as life threatening or emergent as unintended disconnections, water in the tubing and extubations. However, the incidence of these ventilator events can alert management of the need for more education regarding adjusting the ventilator for patient comfort and understanding ventilator waveforms. Events during procedures reminds the health care team that the patients still need to be ventilated during other important procedures being completed at the bedside.

In one embodiment, the program on server 530 is written in Java and listens on a TCP/IP port for messages sent from the bedside computers 515. The bedside and nursing station computers 535 may also "check-in" with server 530 (e.g., every 10 minutes). A program on server 530 contains a table with the nursing units, rooms, and IP addresses of each of the computers. If a computer has not checked-in during the previous hour, that computer is marked as "out of service" and removed from the table. When a computer is replaced or brought back online, a startup message is sent to the server and the current data is loaded into the table. Another program on the server collects and analyzes the data sent from the bedside and nursing station computers. If that computer does not check in with the server every 30 minutes, a message is sent to the pagers of the on-call staff to determine the status of the computer. This process enables the table on the server to contain the correct IP addresses and other information for the computers in each of the units. Thus, when one of the three messages is sent by bedside computer 515, the server program determines which unit the computer is in and searches the table for other computers that are in the same unit. As the server finds computers in the same unit, it then sends the same message over the TCP/IP connection to the computers. For activate alert messages, an alert record is created which includes the patient's encounter number, time of the event and room number and is stored in a key-sequenced file on the EMR hospital information system 525.

In one embodiment, a program loaded on the bedside computers 515 and nursing station computers 535 in the units is also written in Java and runs as a Microsoft Windows service. When this program receives an activate-alert message from the server, it sends a Java frame to the terminal. In one embodiment, the Java frame fills the whole screen and/or the background of the frame alternates between red and black every three seconds (FIG. 2). The room number is displayed large enough to be seen from 20 to 25 feet away. An audio message containing the "submarine dive horn" is also sent to the non-bedside computers in the same unit. The alerts are then sent by email, to pagers and/or to any other communication device, so that respiratory care management is informed of each critical event.

In an exemplary embodiment, turning off the enhanced visual and audio alerts sent to the computers in the unit includes one or more of: 1) correct the event problem at the bedside, 2) press the alarm silence button on the ventilator, and/or 3) close the alert window on the computer. If the healthcare provider closes the alert window on the computer, he or she has to acknowledge and terminate the alert. The program then logs how the alert was turned off and from which computer.

The respiratory therapy charting program on EMR system 525 notifies the healthcare provider whenever an enhanced ventilator alert had been generated for a patient for which they were providing care. In one embodiment, each time the charting program is run, it accesses the key-sequenced file on EMR system 525 and checks for enhanced alerts stored by the program on the server. If the current patient has an undocumented ventilator alert, a window requesting information concerning the event is opened (e.g., when the healthcare provider has finished charting). The healthcare provider is requested to enter information concerning the cause of the event (e.g., unintended disconnection, obstruction caused by water in the tube, disconnection during a procedure, other event, and/or undetermined) and whether the patient was extubated. Other information requested by the program may include describing the patient and the environment during the time of the event such as, for example, prior status of the patient, how the endotrachial tube was secured, the staffing level of the unit, who was in the room, post status of the patient, who was notified of the event, and the ventilator serial number. If the healthcare provider's time is limited due to other patient care needs, the healthcare provider has the option to enter the data the next time they chart on that patient. On some occasions, this notification may be the first time the healthcare providers find out about the event and they may need to contact other medical personnel to collect the requested information. The event information provided by the healthcare provider is coded and now stored in EMR 525, along with the other respiratory therapy information. In addition, this information is sent to a staging file located on the enterprise data warehouse (EDW) 540.

In one embodiment, EDW 540 servers run on Oracle version 9.2.0.3. The data sent to the staging file is loaded into EDW 540. For example, the loading may occur at a particular time early each morning to allow incoming data to be queued, while minimizing the impact on the performance of EDW 540 during peak hours. SQL scripts and processes are used to load the event data into a relational table and retain the EMR system hierarchical codes. A ventilator event report is created using Crystal Reports version 9. To facilitate the development of the report, a view is created that translates the EMR data from a name/value pair structure into a relational structure.

Reports may be available online such that the user is requested to enter the beginning and end date for the report, and select the hospital. Thus, the report can be run monthly, quarterly or ad hoc. In one embodiment, the report displays the number of critical ventilator events by category in both graph and table form. The patient who experienced the event is identified by hospital account number and the permanent enterprise master patient identifier (EMPI) number. For the patients with unintentional disconnections, the detailed information entered by the healthcare providers is also listed. The report also can be used to identify when healthcare providers did not enter ventilator event information when they were prompted by the respiratory charting program.

The video/audio ventilator alerts of the present invention may be very distinct from any other alarms in the ICU, thereby increasing the likelihood that they will be difficult to ignore, thereby minimizing prolonged duration of critical ventilator events. Unless the healthcare provider is charting on a computer, the audio alert is typically noticed first. Although the audio is not sent to the bedside computers, the audio from the nursing stations may be heard in the patient rooms, even when the door is closed.

To avoid additional patient confusion and stress, in one embodiment, the system does not send the audio alerts to the bedside computers. During the daytime, at least one person is typically using one of the computers in the unit. However, during the night shift, this is not true, so the system includes the audio alert as well. This enhanced system is designed to provide effective notification of ventilator events during any time of day or staff configuration.

One item of potential concern is that while healthcare providers may now be more attentive with ventilator management to avoid disturbing the other staff with the enhanced alerts, they may also be tempted to silence the alarm more often during patient procedures. Since there is a ten second delay between the ventilator alarm and the enhanced alert being triggered, healthcare providers know that if they silence the ventilator alarm quick enough, the enhanced alert will not activate. Respiratory care management should monitor this process to make sure that the ventilator silence button is not over used as patient harm can occur during procedures. In addition, if a ventilator alarm is silenced for two or more minutes, the enhanced alert will activate.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; patient data; and/or like data useful in the operation of the system. As those skilled in the art will appreciate, user computer may include an operating system (e.g., Windows NT, 95/98/2000, OS2, UNIX, Linux, Solaris, MacOS, etc.) as well as various conventional support software and drivers typically associated with computers. The computer may include any suitable personal computer, network computer, workstation, minicomputer, mainframe or the like. The computers may be in a hospital, clinic, office, home or business environment with access to a network. In an exemplary embodiment, access is through a network or the Internet through a commercially-available web-browser software package.

As used herein, the term "network" shall include any electronic communications means which incorporates both hardware and software components of such. Communication among the parties may be accomplished through any suitable communication channels, such as, for example, a telephone network, an extranet, an intranet, Internet, point of interaction device (point of sale device, personal digital assistant (e.g., Palm Pilot®, Blackberry®), cellular phone, kiosk, etc.), online communications, satellite communications, off-line communications, wireless communications, transponder communications, local area network (LAN), wide area network (WAN), networked or linked devices, keyboard, mouse and/or any suitable communication or data input modality. Moreover, the system may be implemented with TCP/IP communications protocols, or by using IPX, Appletalk, IP-6, NetBIOS, OSI or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network.

As used herein, "transmit" may include sending electronic data from one system component to another over a network connection. Additionally, as used herein, "data" may include encompassing information such as commands, queries, files, data for storage, and the like in digital or any other form.

The system contemplates uses in association with web services, utility computing, pervasive and individualized computing, security and identity solutions, autonomic computing, commodity computing, mobility and wireless solutions, open source, biometrics, grid computing and/or mesh computing.

Any databases discussed herein may include relational, hierarchical, graphical, or object-oriented structure and/or any other database configurations. Common database products that may be used to implement the databases include DB2 by IBM (White Plains, N.Y.), various database products available from Oracle Corporation (Redwood Shores, Calif.), Microsoft Access or Microsoft SQL Server by Microsoft Corporation (Redmond, Wash.), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

The computing unit of the web client may be further equipped with an Internet browser connected to the Internet or an intranet using standard dial-up, cable, DSL or any other Internet protocol known in the art. Transactions originating at a web client may pass through a firewall in order to prevent unauthorized access from users of other networks. Further, additional firewalls may be deployed between the varying components of CMS to further enhance security.

Firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based and Packet Filtering among others. Firewall may be integrated within an web server or any other CMS components or may further reside as a separate entity.

The computers discussed herein may provide a suitable website or other Internet-based graphical user interface which is accessible by users. In one embodiment, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, Interbase, etc., may be used to provide an Active Data Object (ADO) compliant database management system.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, Java applets, JavaScript, active server pages (ASP), common gateway interface scripts (CGI), extensible markup language (XML), dynamic HTML, cascading style sheets (CSS), helper applications, plug-ins, and the like. A server may include a web service that receives a request from a web server, the request including a URL (http://yahoo.com/stockquotes/ge) and an IP address (123.56.789.234). The web server retrieves the appropriate web pages and sends the data or applications for the web pages to the IP address. Web services are applications that are capable of interacting with other applications over a communications means, such as the internet. Web services are typically based on standards or protocols such as XML, SOAP, WSDL and UDDI. Web services methods are well known in the art, and are covered in many standard texts. See, e.g., ALEX NGHIEM, IT WEB SERVICES: A ROADMAP FOR THE ENTERPRISE (2003), hereby incorporated by reference.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, Macromedia Cold Fusion, Microsoft Active Server Pages, Java, COBOL, assembler, PERL, Visual Basic, SQL Stored Procedures, extensible markup language (XML), with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JavaScript, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "Java Cryptography" by Jonathan Knudson, published by O'Reilly & Associates (1998); (3) "Cryptography & Network Security: Principles & Practice" by William Stallings, published by Prentice Hall; all of which are hereby incorporated by reference.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise in any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

In the foregoing specification, the invention has been described with reference to specific embodiments. However, it will be appreciated that various modifications and changes can be made without departing from the scope of the present invention as set forth in the claims below. The specification and figures are to be regarded in an illustrative manner, rather than a restrictive one, and all such modifications are intended to be included within the scope of present invention. Accordingly, the scope of the invention should be determined by the appended claims and their legal equivalents, rather than by the examples given above. For example, the steps recited in any of the method or process claims may be executed in any order and are not limited to the order presented in the claims.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus. Moreover, where a phrase similar to 'at least one of A, B, and C' is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

The invention claimed is:

1. A method comprising:
   receiving monitor data transmitted from a healthcare monitoring device associated with a patient and a medical apparatus;
   receiving chart data associated with said patient from a healthcare record system, wherein said chart data comprises prescribed programming settings for said medical apparatus;
   retrieving baseline data from a database based at least partially upon at least one of said monitor data or said patient chart data;
   determining decision data violates a rule, wherein said decision data comprises said monitor data, said chart data and said baseline data;
   in response to determining said decision data violates a rule, compiling an alert information packet, wherein said alert information packet includes information related to at least one of said monitoring device or said decision data; and,
   transmitting said alert information packet to multiple communication devices.

2. The method of claim 1, wherein said rule is a pre-established rule.

3. The method of claim 1, wherein said rule includes multiple pre-established rules.

4. The method of claim 1, wherein said step of transmitting said alert information packet to multiple communication devices includes transmitting said alert information packet to multiple computer screens in a particular area, wherein said area is associated with said healthcare monitoring device.

5. The method of claim 1, wherein, said determining said decision data violates said rule, comprises determining said decision data violates a programming rule associated with said monitoring device.

6. The method of claim 1, wherein, said determining said decision data violates said rule, comprises determining said decision data violates a programming rule based on at least one of rate percentage increases or unit specific protocols.

7. The method of claim 1, wherein said healthcare monitoring device includes at least one of an infusion pump or a ventilator.

8. The method of claim 1 further comprising:
   polling said monitoring device for current programming settings;
   in response to said current programming settings being outside of a predetermined variance of said prescribed programming settings, sending an alert to said monitoring device.

9. The method of claim 1, further comprising distinguishing at least one of severity or type of monitor data to reduce false positive alerts.

10. The method of claim 1, further comprising analyzing when an alarm silence code associated with said monitoring device is activated.

11. The method of claim 1, further comprising maintaining a table of in-service computer information for transmission of said alert information packet.

12. The method of claim 1, wherein said transmitting step comprises transmitting said alert information packet to multiple communication devices in a same unit.

* * * * *